United States Patent [19]

Schietinger et al.

[11] Patent Number: 5,166,080

[45] Date of Patent: Nov. 24, 1992

[54] TECHNIQUES FOR MEASURING THE THICKNESS OF A FILM FORMED ON A SUBSTRATE

[75] Inventors: Charles W. Schietinger; Bruce E. Adams, both of Portland, Oreg.

[73] Assignee: Luxtron Corporation, Santa Clara, Calif.

[21] Appl. No.: 692,578

[22] Filed: Apr. 29, 1991

[51] Int. Cl.$^5$ ............................................. H01L 21/00
[52] U.S. Cl. ............................................ 437/7; 437/8; 437/173; 374/7; 374/120; 374/121
[58] Field of Search ............... 374/7, 120, 121; 437/8, 437/926, 7, 173

[56] References Cited

U.S. PATENT DOCUMENTS

| | | | |
|---|---|---|---|
| 4,745,291 | 5/1988 | Niiya . | |
| 4,750,139 | 6/1988 | Dils | 364/557 |
| 4,989,970 | 2/1991 | Campbell et al. | 374/126 |
| 5,048,960 | 9/1991 | Hayashi et al. | 356/319 |

FOREIGN PATENT DOCUMENTS 0118069  5/1990  Japan .

OTHER PUBLICATIONS

Pettibone et al., "The Effect of Thin Dielectric Films on the Accuracy of Pyrometric Temperature Measurement", *Materials Research Society Symposia Proceedings,* vol. 52, pp. 209–216, 1986.

Accufiber, "New Ways to Improve RPT Through Optical Fiber Thermometry", *Application Note,* 16 pages, Jul. 28, 1989.

*Primary Examiner*—Brian E. Hearn
*Assistant Examiner*—Trung Dang
*Attorney, Agent, or Firm*—Majestic, Parsons, Siebert & Hsue

[57] ABSTRACT

The thickness of a thin film on a substrate surface is determined by measuring its emissivity and temperature with a non-contact optical technique and then calculating the film thickness from these measurements. The thickness of the film can be determined by this technique in situ, while it is being formed and substantially in real time, thus allowing the measurement to control the film forming process. This has application to controlling the formation of dielectric and other material layers on a semiconductor substrate in the course of manufacturing electornic integrate circuits, including automatically terminating the process at its endpoint when the layer has reached a desired thickness.

28 Claims, 4 Drawing Sheets

TECHNIQUES FOR MEASURING THE THICKNESS OF A FILM FORMED ON A SUBSTRATE

BACKGROUND OF THE INVENTION

This invention is related to the measurement of the thickness of thin films, such as those grown or deposited in the course of processing a semiconductor wafer to form integrated circuits thereon.

There are numerous processes involving thin films where the thickness of the film must be measured. Usually, it is desired that a new film formed on a substrate have a desired thickness within close tolerances. Other applications involve removal of material from a layer in order to form a thin film having a precise thickness. A major application of thin film technology is found in the manufacturing of integrated circuits, both in silicon semiconductor and gallium arsenide based technology. A typical process of forming integrated circuits on a substrate wafer involves the formation of many films and the removal of films, where it is necessary to know at least when the endpoint of the film formation or removal step has been completed. It is also desirable to be able to monitor and control the process in real time by a technique that does not itself interfere with the process.

Therefore, it is a primary object of the present invention to provide such a film monitoring process having a general utility in various processes where thin films are utilized, such as in the manufacture of integrated circuits.

It is another object of the present invention to provide a technique for measuring the thickness of very thin films with a high degree of accuracy and high resolution.

SUMMARY OF THE INVENTION

These and other objects are accomplished by the various aspects of the present invention, wherein, briefly and generally, the thickness of a film is determined by measuring the emissivity of the film and its supporting substrate, preferably by a non-contact optical technique having a very high resolution. Advantage is taken of emissivity changes that occur as a function of the film's thickness. This is believed to occur because the emissivity being measured is a combination of different emissivities of the film and its underlying substrate, the contribution of the film emissivity to this composite measurement thus being dependent upon its thickness. The preferred optical technique is especially adapted for use with films having a thickness from a few Angstroms to a few thousand Angstroms.

According to a specific aspect of the present invention, the thickness measurement is performed in situ as the film is being formed so that its resulting thickness, rate of formation and similar parameters can be controlled in an efficient manner. The process of forming the film can be automatically controlled as a result of the continuous emissivity measurements. This is of particular advantage in integrated circuit processing techniques for monitoring and controlling the deposition or growth of dielectrics, the deposition of metals and metal compounds, and the formation of other material layers.

Additional objects, advantages and features of the present invention will become apparent from the following description of its preferred embodiments, which description should be taken in conjunction with the accompanying drawings.

DESCRIPTION OF THE PREFERRED EMBODIMENTS

Although the improvements of the present invention have application to many varied processes where the measurement of a thin film's thickness is desired, the examples described below are in the process of forming an integrated circuit. Further, the examples deal with silicon semiconductor processes, but they are equally applicable to germanium, gallium arsenide and any other process where emissivity is a function of film thickness. The improvements of the present invention are particularly advantageous in integrated circuit manufacturing processes since resulting films are extremely thin, on the order of tenths of a micron or less, and must have their thicknesses controlled within very narrow limits.

Figure 1:
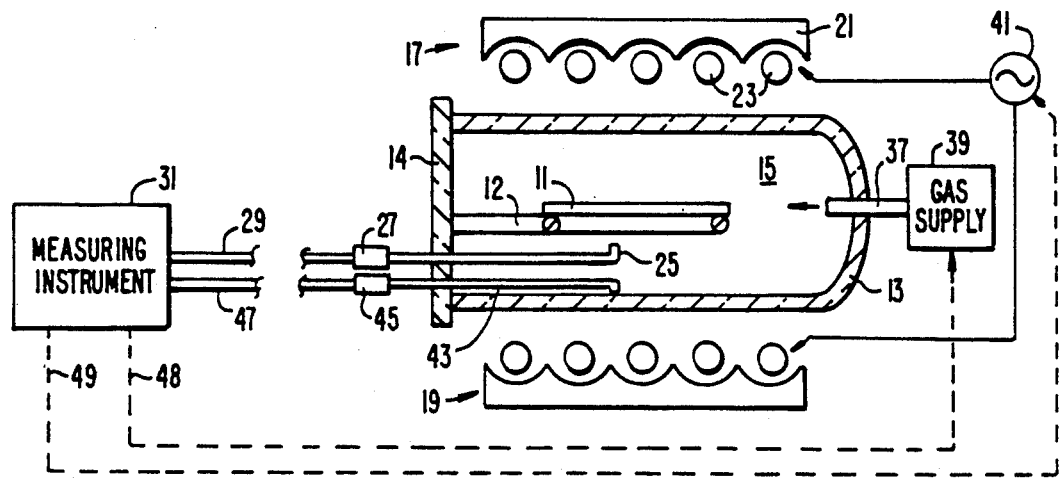
FIG. 1 schematically illustrates a particular type of film forming apparatus that is equipped with a film thickness measuring and control system according to the present invention.

Referring to FIG. 1, a silicon semiconductor substrate 11 is positioned within a substantially optically transparent quartz furnace tube 13. The tube 13 and an end plate 14 form an enclosed chamber 15. The substrate 11 is supported by a quartz support 12 attached to the end piece 14, this support allowing most of the bottom surface of the substrate 11 to be exposed. Of course, there are numerous specific silicon wafer support arrangements and heated process chambers that are used in the industry, the support and process chamber of FIG. 1 being generally shown only for the purpose of explaining the film measurement techniques of the present invention.

The type of semiconductor furnace illustrated in FIG. 1 is that which utilizes lamps external to the chamber 15 for heating the wafer 11. Two such banks of lamps 17 and 19 are illustrated, one on either side of the wafer 11. Each has a plurality of quartz lamps, such as the lamps 23 of the light bank 17, and an appropriate reflector, such as a reflector 21. The lamps are driven by an alternating current power supply 41. Gasses are introduced into the chamber 15 through an inlet 37 from an appropriate source of gas 39. What has been described so far with respect to FIG. 1 is a general outline of a semiconductor reaction chamber which produces strong background radiation in the range of interest for measurement purposes in which the techniques of the present invention may nonetheless be utilized.

One type of film formed in a semiconductor process is a dielectric film. A typical dielectric is a thin silicon dioxide layer that is grown on either the silicon substrate 11 itself or some other layer of silicon based material, such as polysilicon. It is often extremely important to provide such a silicon dioxide film with the designed thickness within very small tolerances. A particular area of concern is during the formation of gate dielectrics, tunnel dielectrics, and others which are extremely thin.

Accordingly, the techniques of the present invention monitor the emissivity of the substrate surface as the film is formed on it. Since the film, having a different composition, has a different emissivity from that of the underlying substrate, the emissivity measured as a thin film is being formed is believed to be a combination of the two. The changing composite emissivity is related to the thickness of the film being formed. A light pipe 25 is positioned within the chamber 15 in order to capture radiation emitted from the bottom surface of the substrate 11 on which the film is being formed. This light pipe is made of some material that can withstand the high temperatures occurring within and adjacent the furnace chamber 15, sapphire being one such material. Because of its refractive index, a sapphire light pipe also has a large numerical aperture (angle of acceptance). Cubic zirconia also has these desirable characteristics. Quartz can alternatively be used as a light pipe material. The light pipe 25 is extended a distance away from the chamber 15 to where the temperatures are cooler, and is there coupled by a connector 27 to a more common fused quartz optical fiber 29. That optical fiber is terminated in a measuring instrument 31.

Not only is the desired optical radiation emission of the substrate and forming film being communicated through the light pipe 25 to the measuring instrument 31, the light pipe 25 is also receiving optical radiation within the same infrared or near infrared radiation band from the bank of lights 19. Therefore, a second light pipe 43 is positioned within the chamber 15 and directed to capture intensity of the heating lamps 19 alone, without any direct optical signal from the substrate or film itself. This light signal is coupled by a connector 45 to an optical fiber 47 and thence provided the measuring instrument 31.

The signals in the optical fibers 29 and 47 are detected by the same type of photodetectors within the measuring instrument 31, and within the same wavelength range. The signal from the light pipe 43 is mathematically manipulated with that from the light pipe 25, thus obtaining a signal related to the optical emission of the substrate and film. That signal is then processed in a manner described below to determine the emissivity of the substrate and film. The thickness of the film is then calculated in real time from the emissivity results. These thickness determinations are then preferably used to control the film forming process, such as by adjusting the power of the lamp driving electrical source 41 through a control circuit 48 and controlling the flow or composition of gasses from the gas supply 39 into the chamber 15 by a signal in a control circuit 49. When the endpoint of a film forming process is detected by calculation of the film thickness reaching its desired magnitude, the power source 41 and/or gas supply 39 will be ramped to the end of the process. In the course of the process before reaching endpoint, the thickness measurement is also used to keep the rate at which the film is formed within specified limits by controlling the lamp power and gas supply.

Figure 2:
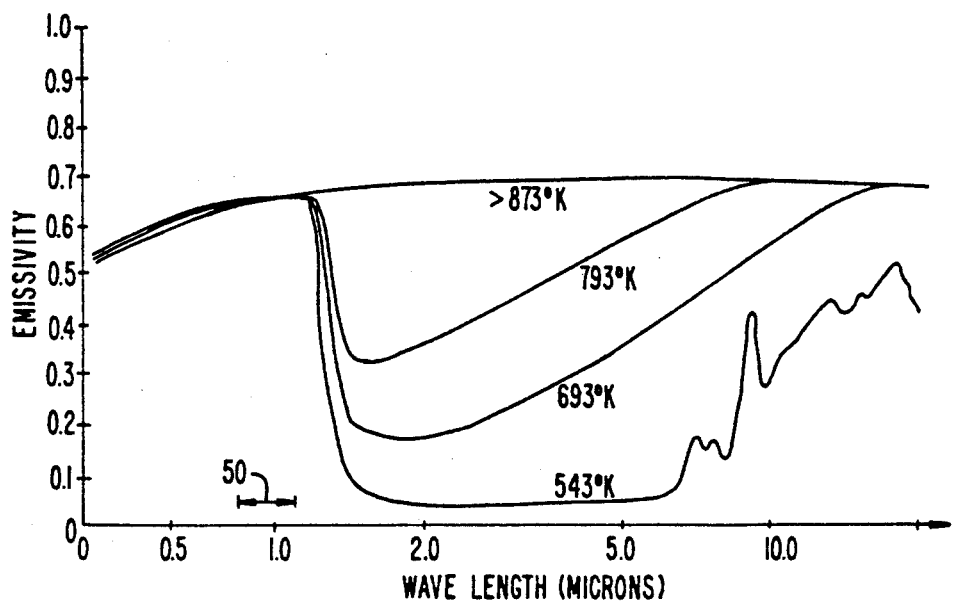
FIG. 2 provides curves that illustrate the emissivity characteristics of one type of substrate upon which a film is controllably formed by the apparatus illustrated in FIG. 1.

Example emissivity characteristics of pure silicon are given in the curves of FIG. 2. A silicon dioxide film being formed on a pure silicon wafer has a different emissivity vs. wavelength characteristic. Since emissivity is also dependent upon the temperature of the substrate and film, a wavelength range of the light pipe 25 optical signal that is detected is preferably that which is the least temperature dependent. Accordingly, a range 50 is illustrated in FIG. 2, extending from about 0.8 to about 1.1 microns, selected to be slightly below the absorption band edge of about 1.2 microns of silicon. As can be seen from FIG. 2, the emissivity of silicon becomes very temperature dependent when observed at wavelengths above that band edge. Other semiconductor materials have different absorption band edges, so the wavelength band selected for these measurements will be different, generally slightly below the band edge.

Since temperature cannot totally be eliminated as a variable by wavelength selection, particularly in a general technique used with different combinations of materials, it is usually desired to also measure temperature of a substrate and film from the optical radiation signal therefrom that is captured by the light pipe 25. Both the emissivity and temperature information is then utilized to calculate film thickness.

Figure 3:
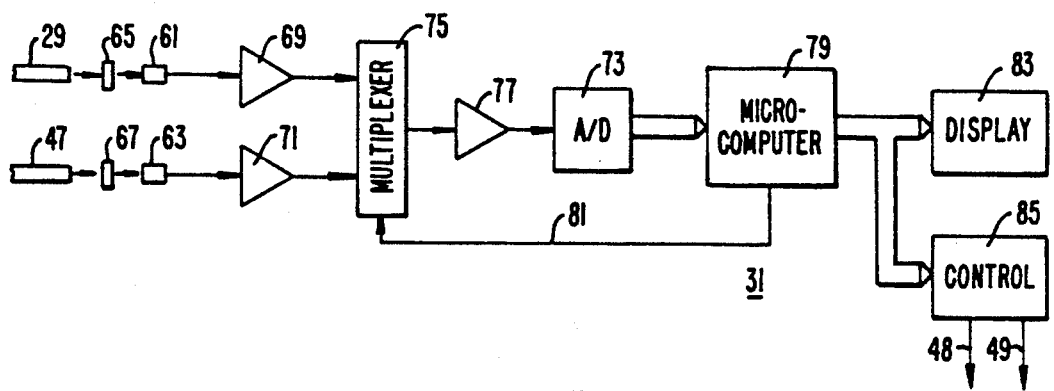
FIG. 3 is a circuit block diagram of the measuring instrument of the apparatus of FIG. 1.

The main functional components of the measuring instrument 31 are illustrated in FIG. 3. A more detailed measuring system for a related application is described in U.S. Pat. No. 4,750,139—Dils (1988). Photodetectors 61 and 63 receive the optical signals from the respective Optical fibers 29 and 47. These signals are first passed through optical filters 65 and 67, respectively. These filters preferably pass the same narrow bandwidth of optical radiation, such as one around 0.95 microns for the specific application being described. The photodetectors 61 and 63 are then preferably a commercially available silicon type.

The electrical signal outputs of the photodetectors 61 and 63 are amplified by respective linear amplifiers 69 and 71. In order to time share a common analog-to-digital converter 73, a multiplexer circuit 75 is provided to alternately connect the outputs of the amplifiers 69 and 71 to another linear amplifier 77, whose output is then provided as an input to the analog-to-digital converter 73. The digitized signals are received by a microcomputer 79 and processed. Part of the controlling function of the microcomputer 79 is to switch the multiplexer 75 by an appropriate control signal in the line 81.

The resulting thickness calculated by the microcomputer 79 from its input signals can either then be displayed on a display device 83 and/or utilized by control circuitry 85 to generate process control signals in the circuits 48 and 49 previously mentioned.

Figure 4:
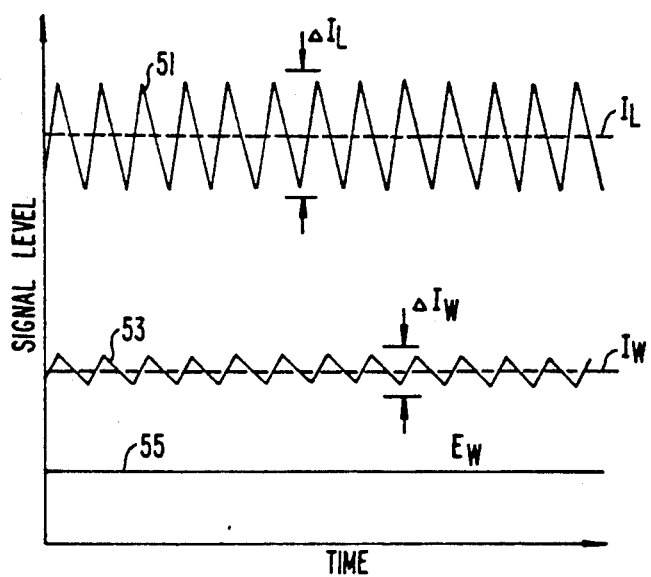
FIG. 4 provides curves to illustrate a specific operation of the apparatus of FIG. 3.
Figure 5:
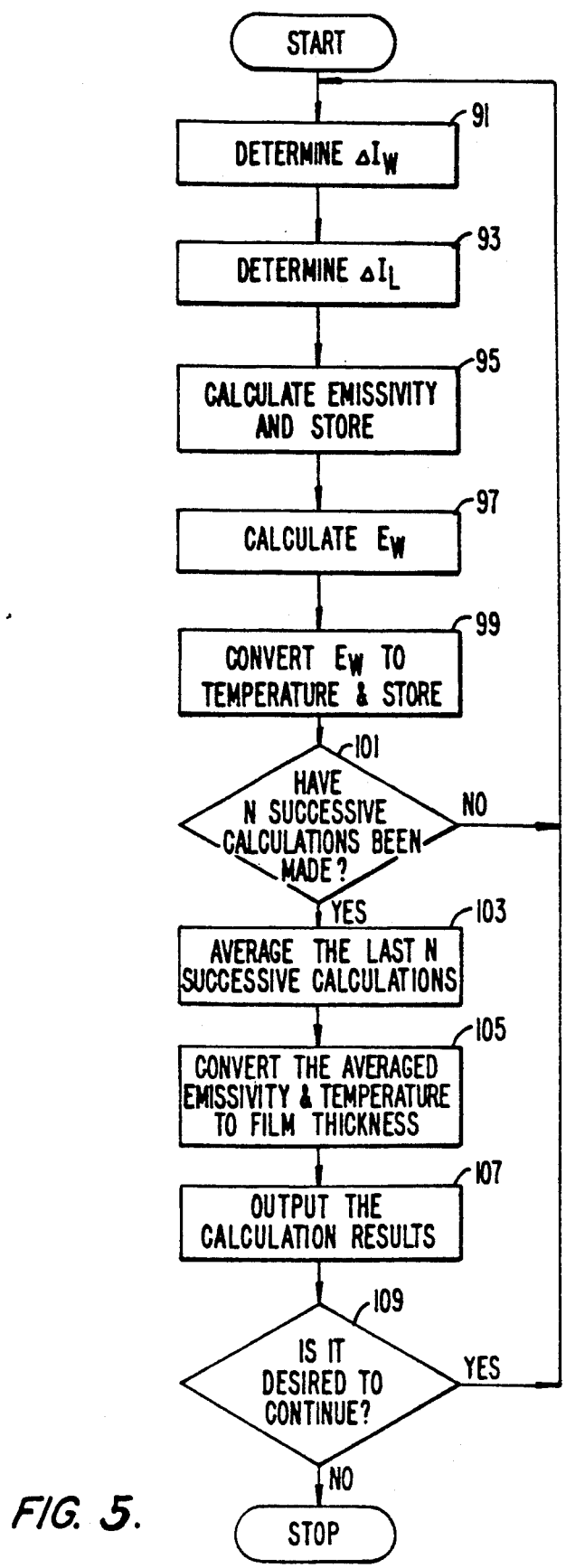
FIG. 5 is a flow chart showing the operation of the micro-computer of the measuring instrument of FIG. 4.

Before describing the calculations performed by the micro-computer 79 with respect to a flow chart of FIG. 5, its processing of the detected optical signals is first illustrated by curves of FIG. 4. A curve 51 shows the signal level output of the detector 63, corresponding to the optical signal of the lamps alone through the light pipe 43. Similarly, a curve 53 illustrates the output of the detector 61 receiving the combined object emission and heating light source reflection received by the light pipe 25. Each of these signals contains a ripple (a.c.) component having a frequency of the power source 41 to the heating lamps, generally 60 Hz. in the United States and 50 Hz. in Europe, but no particular frequency is required for making the thickness measurement. The a.c. component of the signal 51 is indicated by $\Delta I_L$, and the a.c. component of the signal 53 is denoted by $\Delta I_W$. The curves of FIG. 4 also show a steady state signal 55 that is proportional to the emission of the object 11 ($E_W$), which is derived by the micro-computer processing.

Because the light pipes 25 and 43 are selected to have a very large numerical aperture, the following relationship is true.

$$\text{Wafer Reflectivity} = \frac{\Delta I_W}{\Delta I_L} \quad (1)$$

Since we also know that emissivity of an object equals one minus its reflectivity, we can state that:

$$\text{Emissivity} = 1 - \frac{\Delta I_W}{\Delta I_L} \quad (2)$$

Equation (2) provides a measurement of the emissivity of the object. If its temperature is to be measured, the reflected component of $I_W$ can then be subtracted away, leaving the object emission signal alone, as follows:

$$E_W = I_W - I_L \left( \frac{\Delta I_W}{\Delta I_L} \right) \quad (3)$$

Thus, the quantity $E_W$ is solely the thermal emission from the object and thus can be converted into temperature of the substrate and the film being formed on it, by Planck's radiation law. $E_W$ is determined from processing of the d.c. level and a.c. level of the signals 51 and 53. A more detailed description is contained in an accompanying paper to be presented by Schietinger et al, "Ripple Technique: A Novel Non-Contact Wafer Emissivity and Temperature Method for RTP," which is incorporated herein by this reference.

Referring to FIG. 5, the process of the microcomputer 7 in calculating film thickness is illustrated in the form of a flow chart. Initial steps 91 and 93 determine, respectively, the a.c. component of the detected and digitized signals 53 and 51 of FIG. 4. These a.c. components $\Delta I_L$ and $\Delta I_W$ can be determined by directly measuring the peak-to-peak quantities of their respective $I_L$ and $I_W$ signals. Alternatively, a mean value of these signals is first determined and then the area between the alternating curve and this mean value is calculated. A next step 95 is to calculate the emissivity in accordance with Equation (2) above. A next step 97 calculates the steady state quantity 55 of FIG. 4 in accordance with Equation (3) above. That steady state quantity $E_W$ is then converted to temperature of the substrate and film by a reference table or formula empirically determined for the specific substrate and film material compositions being monitored.

At this point, both the emissivity and the temperature of the substrate 11 and film on it have been determined. Since the capabilities of microcomputers allow such calculations to occur at a rapid rate, it is preferable to make the calculations from a large sample of data in quick succession, still within a small fraction of a second, and then average those results before proceeding to calculate the film thickness from them. Thus, a step 101 of the FIG. 5 flow chart keeps track of how many times the emissivity and temperature have been measured and calculated, and will continue to make such calculations until N of them have been made in succession. A step 103 averages the last N calculations. These averages are then utilized in a step 105 to convert the calculated and averaged emissivity and temperature values into film thickness. This conversion takes place by use of either a table or a formula which has been empirically determined for the particular substrate and film compositions being utilized in the process being monitored. That thickness value is then sent to an appropriate output device by a step 107, such as the display 83 or control circuits 85 of FIG. 3.

So long as the monitoring continues, a step 109 then causes the calculation process to go back to the beginning and again calculate the emissivity and temperature a number N times in succession, calculate film thickness therefrom, and so on. The calculation of thickness by the process of FIG. 5 can easily be made within a fraction of a second utilizing an ordinary type of microcomputer 79, thereby allowing the process illustrated in FIG. 1 to be controlled in real time.

Figure 6:
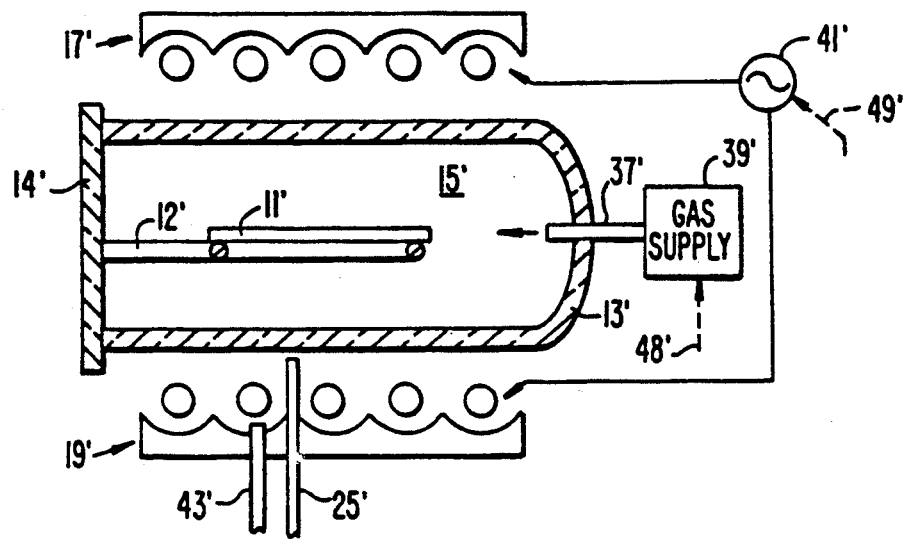
FIG. 6 shows a modified version of the apparatus of FIG. 1.

A modification of the system of FIG. 1 is illustrated in FIG. 6, where corresponding elements and components are identified by the same reference numbers but with a prime (') added. The primary difference is the positioning of light pipes 25' and 43' on the outside of the quartz furnace tube 13'. Thus, the light pipe 25' receives emissions and reflected radiation from the substrate 11' through a wall of the tube 13'. The light pipe 43' receives radiation from an optical lamp without any component from within the furnace tube 13'. The difference in the FIG. 6 arrangement is that the optical signals thus detected are somewhat different than those detected within the chamber 15' by the embodiment of FIG. 1, that difference being a filtering effect caused by the quartz or other material used to make the material 13'.

The example semiconductor processing furnace systems of FIGS. 1 and 6 are of a type utilizing lamps to heat the semiconductor wafers within the processing chamber to the required temperatures where the necessary chemical reactions can take place. This is convenient for application of the techniques of the present invention since a necessary a.c. driven light source already exists. However, there are different techniques for heating semiconductor wafers, such as using a radio frequency generator or resistance heating, where the light source is not available for use in deriving data necessary to make the film thickness calculation. Further, in fields other than in integrated circuit processing, such heating lamps are likely not utilized. In such circumstances, therefore, it is necessary to direct optical radiation against the substrate surface on which a film is being formed.

Figure 7:
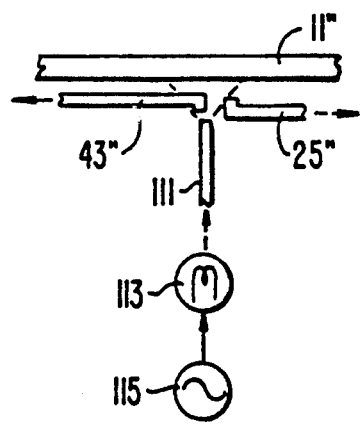
FIG. 7 shows another embodiment of the present invention.

Such a system is schematically illustrated in FIG. 7. An additional sapphire light pipe 111 carries to the subject surface of a substrate 11" optical radiation from a light source 113 that is energized by an alternating current source 115 of any convenient frequency. It may be desired in certain applications to choose a frequency that is distinct from any ambient light having an alternating intensity component. The reflected radiation and emissions from the substrate and film are than gathered by the light pipe 25", corresponding to the light pipe 25 of FIG. 1, and a signal proportional to the intensity of the light striking the substrate 11" is captured by the light pipe 43", corresponding to the light pipe 43 of FIG. 1. Such a system is made practical with the large numerical aperture of the preferred sapphire light pipes.

The wide angle of acceptance of such light pipes results in collecting light that has passed through the film at various different angles, thus traveling through the film with a range of different path lengths. Any variation in intensity level of light passing through the film along any one path that is due to interference effects within the film as it increases in thickness will be different than those variations of light traveling in another path. When all these rays are directed onto a single detector, an averaged signal results which minimizes such interference effects on the emissivity being measured.

Another way to minimize such interference effects is to separately detect in two wavelength bands light passing through the film with a reduced range of angles, such as by directing only central rays of a light pipe onto a photodetector. In the silicon substrate example given above, the second wavelength range would also be less than the 1.2 micron band edge and separated significantly in wavelength from the first range. The bands are kept separate by appropriate beam splitting and filtering with a single pair of light pipes as illustrated herein, or can alternatively utilize an additional pair of light pipes having filters which select the second wavelength band. Also, because of the narrow angle of optical acceptance which is necessary, a traditional optical system, such as a pyrometer, may be substitued for the light pipe.

Yet another way to minimize such interference effects within the film is to separately detect the light passing through the film in at least two different angles with respect to its surface. This can be accomplished by using the large numerical aperture light pipe discussed above but then optically directing its central and outer modes onto different photodetectors. Alternatively, rather than such using a light pipe, two traditional pyrometers may be utilized by directing them at different angles toward the same spot on the substrate surface upon which the film is being formed.

Although the various aspects of the present invention have been described with respect to their preferred embodiments, it will be understood that the invention is entitled to protection within the full scope of the appended claims.

It is claimed:

1. A method of measuring the thickness of a film on a substrate surface, comprising the steps of:
    measuring the emissivity of the substrate surface and film thereon in at least one selected wavelength range, by the steps of:
        directing against said substrate surface and any film thereon optical radiation having a ripple component with a magnitude $\Delta I_L$, thereby to cause optical radiation to be reflected from the surface and combined with optical radiation emitted therefrom, said combined optical radiation having a ripple component with a magnitude $\Delta I_W$,
        detecting the ripple component of the optical radiation being directed toward said substrate surface,
        detecting the ripple component of said combined optical radiation coming from the substrate surface and any of said film thereon, and
        combining said ripple components substantially according to the following relationship:

$$1 - \frac{\Delta I_W}{\Delta I_L};$$

thereby to measure the emissivity of the substrate surface and any of said film thereon, and
    determining the film thickness by reference to a predetermined correspondence between emissivity and the film thickness.

2. The method according to claim 1 wherein the substrate surface and film are characterized by having significantly different emissivities.

3. The method according to claim 1 wherein the emissivity measuring step is caused to occur simultaneously as the film is being formed on the substrate surface, whereby the film thickness determined during its formation may be used to control a process of its formation.

4. The method according to claim 1 wherein said substrate surface exists as part of an electronic integrated circuit wafer being processed.

5. A method of measuring the thickness of a film being formed on a substrate surface, comprising the steps of:
    directing against said substrate surface and any film thereon optical radiation having a magnitude $I_L$ and a ripple component $\Delta I_L$, thereby to cause optical radiation to be reflected from the surface and film, and to be combined with optical radiation emitted therefrom, said combined optical radiation having a magnitude $I_W$ and a ripple component $\Delta I_W$,
    detecting the magnitude and ripple component of the optical radiation being directed toward said substrate surface,
    detecting the magnitude and ripple component of said combined optical radiation coming from the substrate surface and any of said film thereon,
    combining said ripple components substantially according to the following relationship:

$$1 - \frac{\Delta I_W}{\Delta I_L};$$

thereby to measure the emissivity of the substrate surface and any of said film thereon,
    combining said magnitude and ripple components substantially according to the following relationship:

$$I_W - I_L \left( \frac{\Delta I_W}{\Delta I_L} \right);$$

thereby to measure the temperature of the substrate surface and any of said film thereon, and
    determining the film thickness by reference to a predetermined correspondence of the measured emissivity and temperature with film thickness, whereby the film thickness is measured as it is formed on the substrate surface.

6. The method according to claim 5 wherein said substrate surface exists as part of an electronic integrated circuit wafer being processed.

7. As part of a process of manufacturing an electronic circuit structure on a substrate, a method of forming a thin film of material thereon, comprising the steps of:

positioning said substrate structure within a processing chamber, heating said substrate structure, introducing reactive gases into said chamber that cause formation of said film on the heated substrate structure to begin, directing against said film and substrate structure therebeneath optical radiation having a ripple component with a magnitude $\Delta I_L$, thereby to cause optical radiation reflected from the film and structure to be combined with optical radiation emitted therefrom, said combined optical radiation having a ripple component with a magnitude $\Delta I_W$, detecting the ripple component of the optical radiation being directed at said film and structure, detecting the ripple component of said combined optical radiation coming from the film and structure, combining said ripple components substantially according to the following relationship:

$$1 - \frac{\Delta I_W}{\Delta I_L};$$

thereby to measure the emissivity of the film and structure, periodically determining the film thickness by reference to a predetermined correspondence of the measured emissivity with film thickness, whereby the film thickness is measured as it is formed on the substrate structure, and controlling the introduction of reactive gases into said chamber and/or the heating of said substrate structure in response to said periodic film thickness determinations.

8. The method according to claim 7 wherein the controlling step includes terminating introduction of reactive gases into said chamber and termination of heating said substrate structure in response to the film thickness being determined to be a predetermined value.

9. The method according to claim 7 wherein the steps of heating the substrate structure and directing optical radiation with a ripple component thereagainst include use of a set of heating lamps driven by alternating current.

10. The method according to claim 1 wherein the film and substrate include different materials.

11. The method according to any one of claims 1–4 and 10 wherein the ripple component detecting steps each include a step of integrating the detected radiation with respect to respective mean values of the radiation signal.

12. A method of measuring the thickness of a layer one material on a surface of an object of another material, comprising the steps of:

directing electromagnetic radiation toward the layer and object surface in a manner to be modified thereby, said radiation including a given wavelength range and having a periodic intensity ripple, detecting a combined level of the intensity of the given wavelength range of the electromagnetic radiation modified by the layer and object surface and of the intensity of electromagnetic radiation that is emitted from the layer and object surface within the given wavelength range, thereby to generate a first electrical signal having a periodic intensity ripple of a first magnitude, detecting the intensity of a portion of the electromagnetic radiation within said given wavelength range that is being directed toward the layer and object surface, thereby to generate a second electrical signal having a periodic intensity ripple of a second magnitude, and determining the thickness of the layer from at least the first and second electrical signal ripple magnitudes.

13. The method according to claim 12 wherein said object surface includes a semiconductor material, and wherein said given wavelength range lies below an absorption band edge of the semiconductor substrate.

14. The method according to claim 12 wherein at least one of the radiation detecting steps includes the steps of gathering the electromagnetic radiation in a lightpipe made of any one of quartz, sapphire or cubic zirconia, and directing the gathered radiation onto a photodetector.

15. The method according to claim 12 wherein the determining step includes taking a ratio of the ripple magnitudes of said first and second signals.

16. The method according to claim 15 wherein the determining step includes the further step of subtracting said ratio from one, thereby determining a quantity related to emissivity of the layer and object surface.

17. The method according to claim 15 wherein the determining step includes the additional steps of multiplying said ratio by one of said first and second signals and then subtracting the result from the other of said first and second signals, thereby determining a quantity related to temperature of the layer and object surface.

18. The method according to claim 15 wherein the determining step includes the additional steps of multiplying said ratio by the second signal and then subtracting the result from the first signal.

19. The method according to any one of claims 12–18 wherein the detecting steps are accomplished without contacting the object surface.

20. The method according to any one of claims 12–15 wherein the determining step includes the steps of calculating quantities related to an emmissivity and to a temperature of the layer and object surface.

21. In a process of heating an object by directing electromagnetic radiation including a defined bandwidth against at least one surface of the object from a source energized by alternating current, wherein an intensity of the source radiation includes a time varying component, a method of determining a thickness of a layer on said object surface, comprising the steps of:

detecting as a first signal a combined level of radiation emitted from said object surface within a given wavelength range and a portion of said source radiation within said given wavelength range that is reflected from said object surface, said given wavelength range overlapping said defined bandwidth of the source, detecting as a second signal a level of source radiation that is being directed within said given wavelength range against said object surface, determining a magnitude of a time varying component in each of said first and second signals that is the result of said source time varying component, and combining at least the time varying component magnitudes of said first and second signals in a manner to determine said layer thickness.

22. The method according to claim 21 wherein the layer thickness determination is caused to occur substantially simultaneously with formation of the layer on the object.

23. The method according to claim 22 which comprises an additional step of utilizing the layer thickness determination to control a process of forming the layer on the object.

24. The method according to claim 21 wherein said object includes a semiconductor substrate and the layer is a layer of material being utilized to construct an integrated electronic circuit on said substrate.

25. The method according to claim 24 wherein said given wavelength range lies below an absorption band edge of the semiconductor substrate.

26. The method according to claim 21 wherein at least one of the radiation detecting steps includes the steps of gathering the electromagnetic radiation in a lightpipe made of any one of quartz, sapphire or cubic zirconia, and directing the gathered radiation onto a photodetector.

27. The method according to any one of claims 21-26 wherein the determining step includes taking a ratio of the time varying component magnitudes of said first and second signals.

28. The method according to any one of claims 21-26 wherein the determining step includes the steps of calculating quantities related to an emissivity and to a temperature of the object surface and layer thereon.

* * * * *